(12) United States Patent
Valentin et al.

(10) Patent No.: US 11,864,951 B2
(45) Date of Patent: Jan. 9, 2024

(54) PROBE HAVING A COOLING CHAMBER AND METHOD FOR MANUFACTURING SUCH A PROBE

(71) Applicant: SUPERSONIC IMAGINE, Aix en Provence (FR)

(72) Inventors: Matthieu Valentin, Marseilles (FR); Etienne Rousseau, Aix en Provence (FR); Frédéric Giral, Pourcieux (FR)

(73) Assignee: SuperSonic Imagine, Aix-en-Provence (FR)

( * ) Notice: Subject to any disclaimer, the term of this patent is extended or adjusted under 35 U.S.C. 154(b) by 200 days.

(21) Appl. No.: 17/294,444

(22) PCT Filed: Oct. 10, 2019

(86) PCT No.: PCT/FR2019/052412
§ 371 (c)(1),
(2) Date: May 17, 2021

(87) PCT Pub. No.: WO2020/099742
PCT Pub. Date: May 22, 2020

(65) Prior Publication Data
US 2022/0015744 A1 Jan. 20, 2022

(30) Foreign Application Priority Data
Nov. 16, 2018 (FR) ..................................... 18 71577

(51) Int. Cl.
*A61B 18/00* (2006.01)
*A61B 8/00* (2006.01)
*H05K 7/20* (2006.01)

(52) U.S. Cl.
CPC ............ *A61B 8/546* (2013.01); *A61B 8/4444* (2013.01); *H05K 7/20272* (2013.01); *A61B 2018/00011* (2013.01); *H05K 7/20236* (2013.01)

(58) Field of Classification Search
None
See application file for complete search history.

(56) References Cited

U.S. PATENT DOCUMENTS

| 5,560,362 A | 10/1996 | Sliwa et al. |
| 7,314,447 B2 | 1/2008 | Park et al. |

(Continued)

FOREIGN PATENT DOCUMENTS

| EP | 0 782 125 A2 | 7/1997 |
| EP | 1 707 122 A1 | 10/2006 |

(Continued)

OTHER PUBLICATIONS

International Search Report and Written Opinion of the International Searching Authority for International Patent Application No. PCT/FR2019/052412 dated Mar. 13, 2020, 12 pages.

(Continued)

*Primary Examiner* — Courtney L Smith
(74) *Attorney, Agent, or Firm* — Merchant & Gould P.C.

(57) ABSTRACT

The invention relates to a probe (110, 210, 310, 410, 510) which has a sealed cooling chamber (140, 240, 340, 440, 540) arranged within a casing (112, 212, 312, 412, 512) of the probe. An interface unit (124, 224, 324, 424, 524) of the probe is at least partially arranged within the cooling chamber or in contact with the cooling chamber. The cooling chamber is at least partially filled with a heat transfer liquid (142, 242, 342, 442, 542).

18 Claims, 3 Drawing Sheets

(56) References Cited

U.S. PATENT DOCUMENTS

| | | | |
|---|---|---|---|
| 10,314,560 B2* | 6/2019 | Havel | A61B 8/0891 |
| 11,103,136 B2* | 8/2021 | Hashimoto | A61B 8/546 |
| 11,540,814 B2* | 1/2023 | Clark | A61B 8/4444 |
| 2008/0146924 A1 | 6/2008 | Smith et al. | |
| 2008/0188755 A1 | 8/2008 | Hart | |
| 2009/0234230 A1 | 9/2009 | Bercoff et al. | |
| 2011/0077555 A1* | 3/2011 | Wing | A61B 8/546 |
| | | | 601/2 |
| 2012/0060610 A1* | 3/2012 | Oaks | A61B 8/4444 |
| | | | 73/632 |
| 2013/0190661 A1* | 7/2013 | Wing | A61B 8/546 |
| | | | 601/3 |
| 2014/0107489 A1* | 4/2014 | Fearnot | A61B 8/4461 |
| | | | 600/463 |
| 2016/0041129 A1 | 2/2016 | Cho et al. | |
| 2017/0172402 A1 | 6/2017 | Wakabayashi | |

FOREIGN PATENT DOCUMENTS

| | | |
|---|---|---|
| FR | 2 910 169 A1 | 6/2008 |
| WO | 2016/162855 A1 | 10/2016 |
| WO | 2020/118131 A1 | 6/2020 |

OTHER PUBLICATIONS

Liu, Y. et al., "Heat transfer performance of lotus-type porous copper heat sink with liquid GaInSn coolant", International Journal of Heat and Mass Transfer, 80: 605-613 (2015).

Oguntala, G. et al., "Numerical Investigation of Inclination on the Thermal Performance of Porous Fin Heatsink using Pseudospectral Collocation Method", Karbala International Journal of Modern Science, 5(1): 19-26 (2019).

"Low Profile Metallic Foam Heat Sinks", Versarien Technologies®, 3 pages (2015).

\* cited by examiner

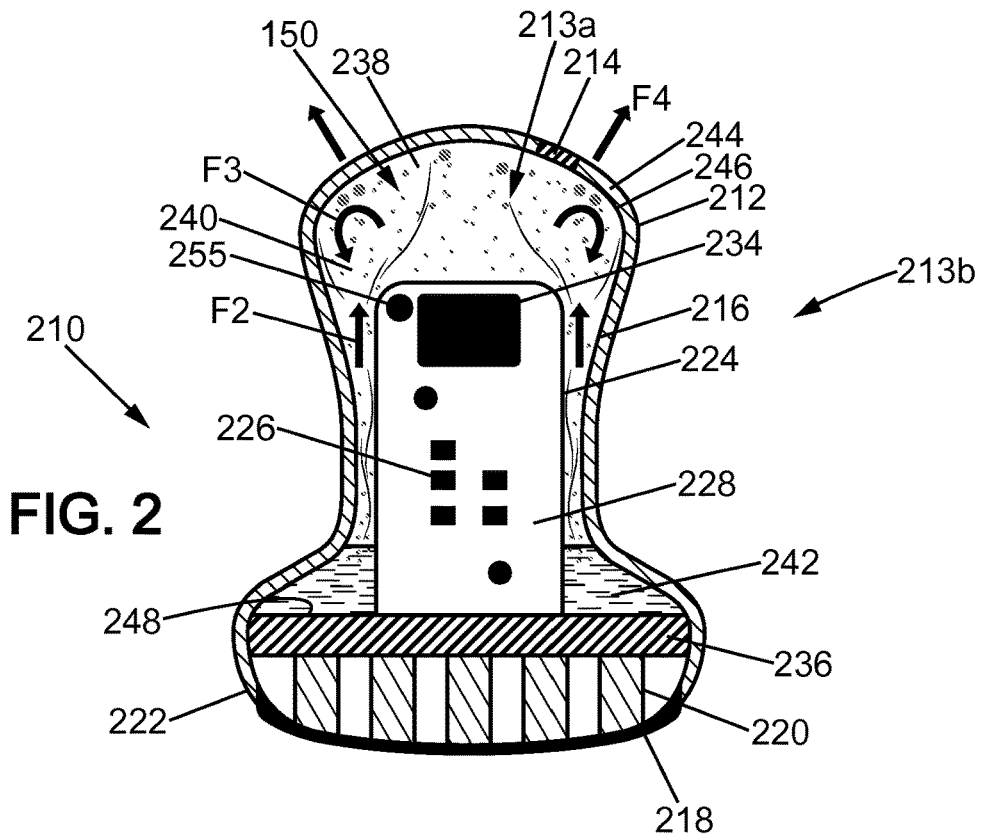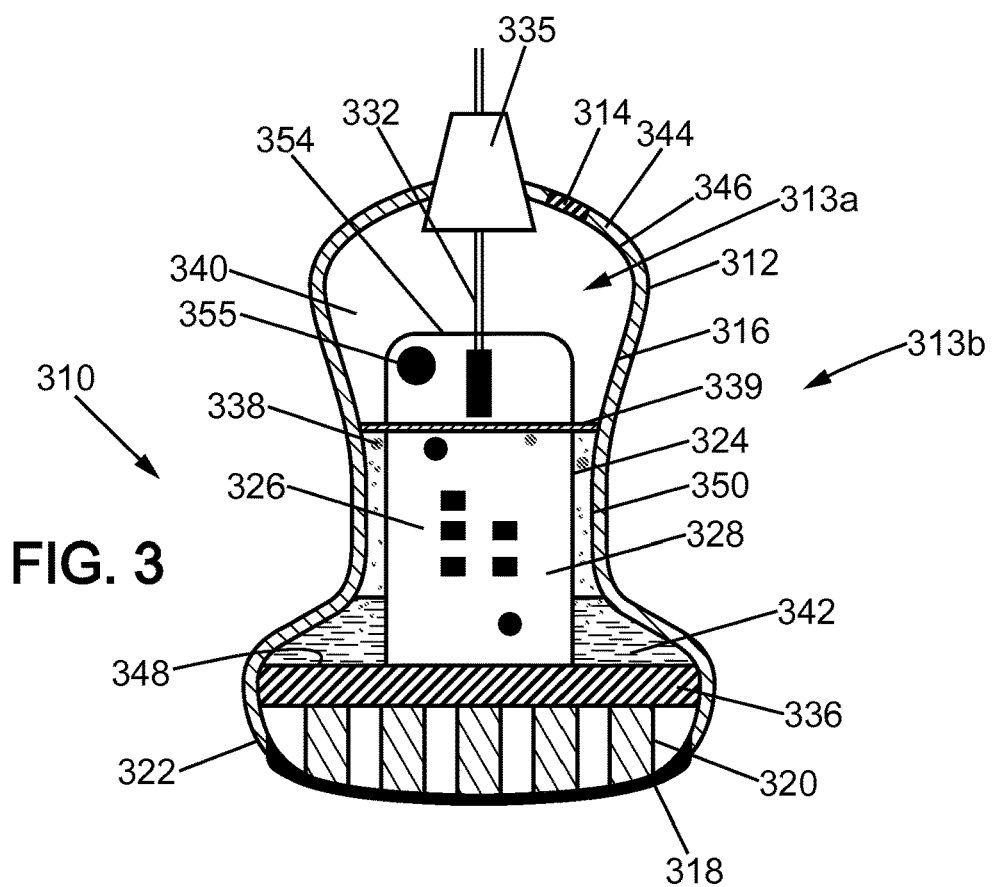

PROBE HAVING A COOLING CHAMBER AND METHOD FOR MANUFACTURING SUCH A PROBE

This application is a National Stage Application of PCT/FR2019/052412, filed 10 Oct. 2019, which claims benefit of Application Serial No. 18 71577, filed 16 Nov. 2018 in France, and which applications are incorporated herein by reference. To the extent appropriate, a claim of priority is made to each of the above disclosed applications.

TECHNICAL FIELD

This invention relates to probes, in particular probes for ultrasound.

PRIOR ART

More particularly, the invention relates to a probe which can be part of an ultrasound imaging system.

Ultrasound imaging works by emitting ultrasonic waves into a medium and recording the ultrasonic waves reflected by the medium.

For this purpose, a probe is used to position the emitting/receiving elements for waves at the organ to be imaged. The waves are created by actuators, for example of the piezoelectric or cMUT type which during operation produce induced heat. This heat can be a function of the power of the emitted waves. US patent application 2009/234230 shows an example of a probe emitting at a high frequency.

This heat can sometimes reach a temperature which can be uncomfortable for the patient and/or not in compliance with the standards in force for medical equipment. In addition, an increase in temperature in the probe can temporarily or permanently reduce its capabilities.

Mechanisms are sometimes provided to prevent the probe from being damaged, for example when a certain temperature is reached the power of the probe can be restricted in order to protect its internal components. For example, the threshold temperature can be between 50° C. and 80° C. The probes can also be programmed to shut off when this threshold temperature is reached, to allow the probe to cool. In addition, such heating can limit the rate of the ultrasound sequences emitted from the probe to create images.

DISCLOSURE OF THE INVENTION

The object of the invention is to improve probes of the type mentioned below, in order to prevent excessive heating of the probe or even damage to it.

The invention thus relates to a probe which comprises:
a casing defining an interior of the probe,
one or more emitting and/or receiving elements for acoustic waves, arranged at a first end of the probe,
an interface unit connected to the emitting and/or receiving element, the interface unit being located within the interior of the casing,
characterized in that the probe comprises a sealed cooling chamber arranged within the interior of the casing, the interface unit being arranged at least partially in the cooling chamber or in contact with the cooling chamber, the cooling chamber being at least partially filled with a heat transfer liquid.

Due to the presence of the cooling chamber, the temperature of the probe during operation can be effectively reduced without requiring the probe to be turned off.

During operation, the plurality of emitting and/or receiving elements for acoustic waves produces heat, and the heat transfer liquid displaces this heat towards a second end of the probe, the second end being distal to the plurality of emitting and/or receiving elements for acoustic waves.

In various embodiments of the probe according to the invention, recourse may also optionally be made to one or more of the following arrangements.

According to one aspect, the heat transfer liquid is dielectric.

According to one aspect, the heat transfer liquid is phase changing, and has a transition temperature that is a function of the temperature resulting from the heat produced by the emitting and/or receiving element for acoustic waves during operation.

According to one aspect, the transition temperature of the heat transfer liquid is between room temperature and a temperature of 90 degrees Celsius.

According to one aspect, the cooling chamber is filled with the heat transfer liquid and a gas.

According to one aspect, the portion of the cooling chamber filled with the heat transfer liquid represents at least 5% of the volume of the cooling chamber.

According to one aspect, a pressure sensor and/or a temperature sensor is within the interior of the probe.

According to one aspect, an acoustic-wave-blocking element is arranged between the interface unit and said at least one emitting and/or receiving element for acoustic waves, the cooling chamber being in contact with the wave-blocking element.

According to one aspect, an acoustic-wave-blocking element is arranged between the interface unit and said at least one emitting and/or receiving element for acoustic waves, the cooling chamber being defined by a rear face of the wave-blocking element and by an inner wall of the casing.

According to one aspect, the interface unit is completely contained within the cooling chamber.

According to one aspect, the interface unit comprises an antenna.

According to one aspect, the interior of the probe comprises a dry chamber separate from the cooling chamber, the cooling chamber being proximal to the first end of the probe.

According to one aspect, a portion of the interface unit is arranged in the dry chamber.

According to one aspect, the sealed cooling chamber comprises at least one flexible portion.

According to one aspect, the cooling chamber comprises two flexible pouches at least partially filled with the heat transfer liquid.

The invention also relates to a method of manufacturing a probe, in particular for ultrasound, the probe being in particular as stated above. The method comprises the following steps:
a casing is provided to define an interior of the probe,
one or more emitting and/or receiving elements for acoustic waves are provided and they are placed at a first end of the casing,
an interface unit is provided and it is connected to the emitting and/or receiving element(s), the interface unit is placed within the interior of the casing,
the casing is sealed closed to form a sealed cooling chamber arranged within the interior of the casing, the interface unit being at least partially arranged in the cooling chamber or in contact with the cooling chamber, and
the cooling chamber is at least partially filled with a heat transfer liquid.

In various embodiments of the method according to the invention, recourse may possibly be made to one or more of the following arrangements.

According to one aspect, the cooling chamber is filled with the heat transfer liquid and a gas.

According to one aspect, the last two steps of the method are carried out by the following successive steps:
- a flexible pouch at least partially filled with the heat transfer liquid is placed in the casing, and
- the casing is sealed closed to form the sealed cooling chamber.

BRIEF DESCRIPTION OF DRAWINGS

Other features and advantages of the invention will become apparent from the following description of one of its embodiments, given as a non-limiting example, with reference to the accompanying drawings.

In the drawings:

FIG. 2 is a front sectional view of a probe according to a second embodiment;

FIG. 3 is a front sectional view of a probe according to a third embodiment;

In the various figures, the same reference numbers designate identical or similar elements.

DETAILED DESCRIPTION

Figure 1A:
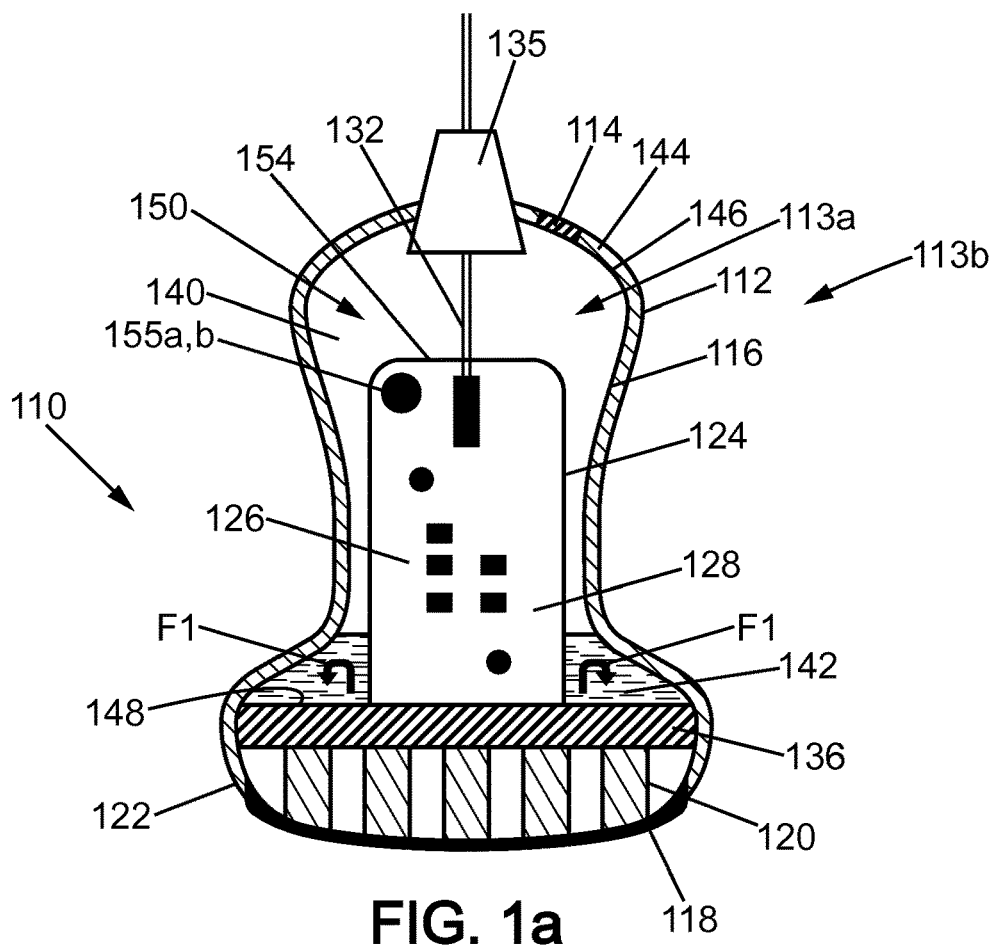
FIG. 1a is a front sectional view of a probe according to a first embodiment.

With reference to FIG. 1a, a probe 110 will be described, in particular for acoustic waves, for example ultrasonic waves. In one embodiment, the probe 110 is part of an ultrasound imaging system. This system may for example be used in a medical context for visualizing organs and/or tissues. To this end, the probe 110 allows the emitting and/or receiving of ultrasonic waves.

The probe 110 includes a casing 112 which is a shell enclosing the various components of the probe 110. The casing 112 defines the boundary between the interior 113a and the exterior 113b of the probe 110. The casing 112 is for example generally rigid to facilitate handling the probe 110. The casing 112 includes a generally ergonomic grip portion 116 by which a user manipulates the probe with one hand. The casing 112 is further composed of an emitting and/or receiving surface 118 which is adapted to be in contact with tissue, for example the skin, or else a wave-transmitting medium, for example such as an ultrasound gel. The emitting and/or receiving surface 118 is shown in the figures as being generally flat, or with a slight curvature, planar or in 2D. However, the emitting and/or receiving surface 118 can have various 3D shapes, possibly with a pronounced curvature. The casing 112 is made of one or more electrically insulating materials, for example such as plastic, for example of the ABS type. The casing 112 may be composed of several assembled parts. For example, the casing 112 (without the emitting and/or receiving surface 118) could be composed of a shell made of a single piece of plastic leaving an opening suitable for receiving the emitting and/or receiving surface 118 therein, thus connected and closing off the casing 112. The casing 112 may be rigid or flexible, in whole or in part. According to one example, the emitting and/or receiving surface 118 is composed of one or more flexible polymer(s).

The probe 110 includes, in the interior 113a of the casing 112, a plurality of emitting and/or receiving elements 120 for acoustic waves, arranged at a first end 122 of the probe 110. Alternatively, it is possible for the probe 110 to comprise a single emitting and/or receiving element 120, but for simplification, this term will be used in the plural in the description. The first end 122 is an end of the probe 110 which comprises the emitting and/or receiving surface 118 of the casing 112. According to one embodiment, the plurality of emitting and/or receiving elements 120 comprises a plurality of piezoelectric elements (a single piezoelectric element in the variant presented above). The plurality of emitting and/or receiving elements 120 may be arranged to form an emission line or leading edge, or else an emission surface.

The plurality of emitting and/or receiving elements 120 is connected to an interface unit 124 which is located within the interior 113a of the probe 110, so as to transmit emission commands and/or receive reception data and communicate with a control unit of the ultrasound imaging system. The interface unit 124, illustrated according to one embodiment in FIG. 2, includes for example two printed circuits 128, each having one or a plurality of electronic components 126, active and/or passive, depending on the embodiments. The printed circuits could alternatively be rigid or flexible. The interface unit 124 may comprise more or less active electronic components (i.e. that require power to operate), such as a battery, one or more pulsers, an antenna, and/or a microprocessor. According to one embodiment, the interface unit 124 is composed only of connector-type passive elements, and constitutes an information relay with the control unit of the imaging system. According to another embodiment, the interface unit 124 comprises active elements and at least partially participates in the creation of emission commands to be sent to the plurality of emitting and/or receiving elements 120. Alternatively, part of the control unit of the imaging system can be relocated to the interface unit 124. According to another embodiment, the interface unit 124 does not include active electronic circuits. In this case, the interface unit is a structure which allows grouping the coaxial cables and making the connection to the emitting and/or receiving elements 120, for example by means of one or more connectors and/or multiplexers.

The printed circuits 128 in this embodiment are generally separated by a heat sink 130. The heat sink 130 is a heat convector. It is for example made of an aluminum plate. According to another embodiment, the interface unit 124 has only one printed circuit, at least two printed circuits 128, and/or does not have a heat sink 130.

In one embodiment, the interface unit 124 communicates with an ultrasound imaging system (not shown) by means of a plurality of coaxial cables 132. In a variant, the coaxial cables 132 are bundled together in a sheath that is fluidtight to the heat transfer liquid 142. For example, the sheath is made of a resin, such as an epoxy. Alternatively, the communication is wireless and the interface unit 124 can comprise an antenna 234 as illustrated in FIG. 2. As a result, this alternative does not in principle include coaxial cables 132. In the embodiment illustrated in FIG. 1a, the coaxial cables 132 pass through the casing 112 via a fluidtight port 135. In the embodiment of FIG. 1a, the fluidtight port 135 is at a second end 144 of the probe 110, the second end 144 being distal to the plurality of emitting and/or receiving elements for acoustic waves 120. The fluidtight port 135 which the coaxial tubes pass through may alternatively be located elsewhere in the casing 112.

The interface unit 124 is separated from the plurality of emitting and/or receiving elements 120 by a wave-blocking element 136 connected to the plurality of emitting and/or receiving elements 120. The wave-blocking element 136 provides at least partial acoustic damping between the plurality of emitting and/or receiving elements 120 and a portion of the interior 113a of the probe 110. Indeed, when the plurality of emitting and/or receiving elements 120 is in operation, the acoustic waves created can propagate towards the interior 113a of the probe 110 and bounce off the various elements located inside the probe, thus creating undesirable acoustic noise. The wave-blocking element 136 is intended to block a large majority of these waves propagating towards the interior 113a of the probe 110, by either returning or absorbing them. The wave-blocking element 136 further allows shortening the duration of the emission pulse. The wave-blocking element 136 is, for example, an elastomer, a flexible resin, or a composite foam. The wave-blocking element 136 may also or alternatively be chosen to be a thermally conductive element.

The probe 110 further includes one (or more in other embodiments) cooling chamber 140 for cooling the probe 110 heated by the operation of the plurality of emitting and/or receiving elements 120. The cooling chamber 140 comprises a heat transfer liquid 142 which at least partially fills it. The cooling chamber 140 is fluidtight to the fluids inside the casing 112, in particular to the heat transfer liquid and/or to the gas if the latter is present in the interior 113a of the casing 112. The cooling chamber may or may not be coincident with a portion of the casing 112. The interface unit 124 is arranged at least partially in the cooling chamber 140 or in contact with the cooling chamber 140. The wave-blocking element 136 may be in contact with the exterior of the cooling chamber 140, or may form a wall thereof. Several non-restrictive examples, presented for illustrative purposes, of cooling chambers 140 and their arrangement relative to the interface unit 124 and the casing 112 are further illustrated with reference to FIGS. 2 to 6.

In the embodiment of FIG. 1a, the cooling chamber 140 is coincident with an interior 113a of the casing 112. The cooling chamber 140 is therefore defined by an inner wall 146 of the casing 112, 212 and by a rear face 148 of the wave-blocking element 136 (the front face of the wave-blocking element 136 being in contact with the plurality of emitting and/or receiving elements 120). The wave-blocking element 136 is fluidtight, so that the heat transfer liquid 142 does not enter the first end 122 of the probe 110 containing the plurality of emitting and/or receiving elements 120. According to other alternatives, the cooling chamber 140 may not be in direct contact with the rear face 148 of the wave-blocking element 136. An intermediate sealing element could for example be arranged there.

During operation, the plurality of emitting and/or receiving elements for acoustic waves 120 produce heat, and the heat transfer liquid 142 transfers an amount of this heat towards the second end 144 which is a zone naturally cooler than the zone of the plurality of emitting and/or receiving elements 120, which has the effect of cooling the probe 110. It is possible to obtain cooling of the probe 110 by means of various characteristics of the heat transfer liquid 142. For example, the cooling may be done by convection/conduction in the liquid itself as illustrated in FIG. 1a or else by convection/conduction and phase changing as illustrated in FIG. 2, the two modes being described below.

In the example illustrated in FIG. 1a, the cooling chamber 140 is partially filled with heat transfer liquid 142, such that another portion of the cooling chamber 140 is filled with a gas 150. The gas 150 is a compressible gas, for example air. According to one embodiment, the cooling chamber 140 is entirely filled with thermally convecting heat transfer liquid 142. According to one embodiment, the cooling chamber 140 is filled with 45% heat transfer liquid 142 and 55% gas 150, by volume. According to one embodiment, the cooling chamber 140 is predominantly filled with heat transfer liquid 142 and the remainder of the volume of the cooling chamber 140 is filled with gas 150.

According to one embodiment, the cooling chamber 140 is filled with heat transfer liquid 142 to at least 5% and conversely with gas 150 up to a maximum of 95%, by volume. According to one embodiment, the cooling chamber 140 is filled with heat transfer liquid 142 to at least 10% and conversely with gas 150 to a maximum of 90%, by volume. The fill percentage may depend on the nature of the heat transfer liquid 142 and/or of the gas 150 and/or of the cooling chamber 140 and/or of any element of the probe. This fill percentage can be optimized by tests.

In the embodiments where the cooling chamber 140 comprises gas 150, it is possible that a part 114 of the cooling chamber 140 (which may or may not be a part of the casing 112 depending on the embodiments) is flexible, so as to serve as a compensation membrane. The compensation membrane 114 can be used whenever the cooling chamber is not completely filled with heat transfer liquid 142. In some variants, it is possible to dispense with the compensation membrane 114 if the walls of the cooling chamber (the casing 112 or other element depending on the embodiments) have sufficient flexibility.

In the example of FIG. 1a, the heat transfer liquid 142 transfers all or part of the heat from the interface unit 124 and/or from the wave-blocking element 136 (therefore indirectly from the plurality of emitting and/or receiving elements 120) towards the second end 144, by convection/convection with no phase change. The particles of the heat transfer liquid 142 heated during operation of the plurality of emitting and/or receiving elements 120 move towards a cooler zone of the heat transfer liquid 142, typically towards the zone of the heat transfer liquid 142 that is furthest from the plurality of emitting and/or receiving elements 120. During this movement, the cooler particles are pushed in the direction of the plurality of emitting and/or receiving elements 120. They are then heated in turn by the heat given off by the plurality of emitting and/or receiving elements 120 during operation, and a circular heating and cooling movement of the particles of the heat transfer liquid 142 is thus produced, as illustrated by the arrows F1. The heat transfer liquid 142 is, for example, water, oil, an alcohol, an ether, a fluorocarbon, or any mixture of these preceding compounds.

Alternatively, the heat exchange may take place by thermal conduction, in the absence or presence of the circular motion presented above. This could be the case when the heat transfer liquid 142 is in a more or less viscous or even gelled form. The envisaged heat transfer liquid 142 thus has various viscosities, which can range from a very low viscosity liquid to a highly viscous liquid or even a gel, at room temperature. The heat transfer liquid 142 is therefore non-solid and non-gaseous within a normal operating range of use. For example, the temperature of use of the probe can vary between 5° C. and 35° C.

Alternatively, the heat exchange may take place by thermal convection. In this case, the heat transfer liquid 142 can advantageously have a viscosity of between 0.32 cSt to 0.8 cSt in order to encourage said convection.

According to one embodiment, the heat transfer liquid 142 is dielectric. When the heat transfer liquid 142 is dielectric, the interface unit 124 in its entirety can be located in the cooling chamber 140, and in particular the parts 154 connecting to the coaxial cables 132 when they exist. Although the heat transfer liquid 142 is illustrated in FIG. 1a as being in contact with part of the interface unit 124, alternatively it is possible that the dielectric liquid is in contact with the entire interface unit 124, such that the interface unit 124 is submerged in the heat transfer liquid 142. This is the case, for example, when the cooling chamber 140 is filled exclusively with heat transfer liquid 142. According to one embodiment, the heat transfer liquid 142 is the liquid 3M™ Novec™ 7000, or a hydrofluoroether (HFE), or a perfluorocarbon (PFC). It is for example possible to decrease the temperature of the probe 110 by 3.5 degrees Celsius after 45 min of use of the probe 110 by using the liquid 3M™ Novec™ 7000 as the heat transfer liquid.

A heat transfer liquid 142 is preferably chosen for which the boiling point is close to the internal temperature of the interior 113a.

A heat transfer liquid 142 is preferably chosen which is compatible with the elements of the probe 110 with which it is in contact, so as not to degrade these elements.

Figure 1B:
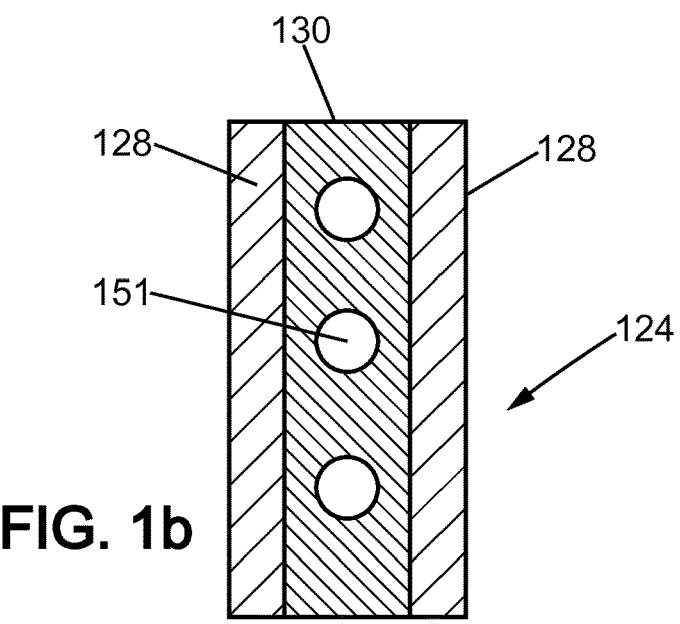
FIG. 1b is a side view of an interface unit of a probe.

Alternatively, it is conceivable that the interface unit 124 has cooling channels 151 passing through the heat sink 130, as illustrated in FIG. 1b, allowing the cooling of the interface unit 124 to be increased. In this embodiment, the heat transfer liquid 142 flows in the cooling channels 151 through the heat sink 130, thus facilitating the heat exchange between the heat transfer liquid 142 and the interface unit 124. The cooling channels 151 can vary in their cross-sectional area and number.

According to one embodiment, the probe 110 further comprises a pressure sensor 115a in the cooling chamber 140, and/or a temperature sensor 155b which may be located in the cooling chamber 140 or elsewhere within the interior 113a of the probe 110. The pressure sensor 155a may for example be located on one of the printed circuits 128, and the temperature sensor 115b on the wave-blocking element 136. The at least one pressure sensor 115a and/or the at least one temperature sensor 155b may be operatively connected to at least one of the printed circuits 128 in order to relay information to the control unit of the ultrasound system. The pressure sensor 115a can be used when the cooling chamber 140 contains gas 150, in order to detect possible leaks of gas 150 or liquid 142 or malfunctions of the system. The temperature sensor 115b makes it possible in particular to detect whether the probe 110 has reached a temperature above a threshold which causes a contact temperature of the probe with the patient's skin that is greater than 43° C.+/−3° C. according to standard IEC60601-1. In the event of an malfunction of the probe, detected by one or more sensors (for example leak of liquid or gas and/or too high of a temperature), an alarm can be activated, it then being possible to restrict the operation of the probe 110 or even shut it off. According to one embodiment, the probe 110 comprises at least one pressure sensor 115a and one temperature sensor 115b which, by combining their information, can be used to detect any leaks of heat transfer liquid 142 during operation of the probe 110.

According to another embodiment and as illustrated in FIG. 2, a probe 210 may have similar characteristics and alternatives to the probe 110 of the first embodiment. This includes in particular the use of a phase-changing heat transfer liquid 242 with a liquid-gas phase change. For brevity, the common characteristics of probes 110 and 210 will have the same reference numbers except numbered in the 200s and will not be repeated here. Probe 210 also differs in particular from probe 110 in that it does not contain a fluidtight port 135 nor coaxial cables 132, the interface unit 224 communicating wirelessly with the control unit of the ultrasound imaging system by means of the antenna 234.

The heat transfer liquid 242 can be chosen to have a boiling point (or transition temperature) close to the local temperature inside the probe 210 when the plurality of emitting and/or receiving elements 220 are in operation. For example, the phase-changing heat transfer liquid 242 can be selected to have a boiling point close to a local temperature of the wave-blocking element 236 or of the interface unit 224. According to one embodiment, the transition temperature of the heat transfer liquid 242 is between room temperature and 90° C. (degrees Celsius), and in particular 34 degrees Celsius. When the wave-blocking element 236 reaches the phase transition temperature, the liquid boils. The gas 238 thus generated (which can be gas 250 or some other gas) moves in the direction of the second end 244 which is naturally cooler than the zone of the probe 210 where the heat transfer liquid 242 is located (arrow F2). Contact with this cooler zone condenses the gas 238 which is converted to droplets of heat transfer liquid 242 and which joins the first end 222 by liquid flow, thus joining the heat transfer liquid 242 not yet evaporated (arrow F3). Some of the heat optionally escapes through the casing 212 at the second end 244 (arrow F4). The gas 250 present in the cooling chamber 240 can have the same characteristics and alternatives as the gas 150 described with reference to FIG. 1a.

Referring to FIG. 3, a third embodiment of the probe 310 is similar to probes 110 and 210, and has the alternatives shown for probes 110 and 210. For brevity, the features that probes 310 have in common with probes 110 and 210 will have the same reference numbers but in the 300s and will not be repeated here. In the embodiment of FIG. 3, the probe 310 further comprises a dry chamber 352. The dry chamber 352 is sealed off from the cooling chamber 340 containing the heat transfer liquid 342. This embodiment can advantageously be used to avoid placing a connection 354 of the coaxial cables 332 within the cooling chamber 340. Thus, in this embodiment, the cooling chamber 340 is located generally towards the first end 322 of the probe 310, and the dry chamber 352 towards the second end 344, the dry chamber then being able to contain a portion of the interface unit which contains the connections 354 of the coaxial cables 332. The interface unit 324 is then located partially in the dry chamber 352 and partially in the cooling chamber 340, the two chambers being separated by a wall 339. In the example illustrated in FIG. 3, only the portion of the interface unit 324 which contains the connections 354 to the coaxial cables 332 is located in the dry chamber 352. However, it is possible that a larger portion of the interface unit is located in the dry chamber 352. Similarly to the example in FIG. 2, in some variants it is possible that the probe 310 does not have coaxial cables 332 or a fluidtight port 335.

As discussed above for FIGS. 1a and 2, the heat transfer liquid 342 may or may not be phase-changing, and may completely or partially fill the cooling chamber 340. As the interface unit 324 is in direct contact with the heat transfer liquid 342, the heat transfer liquid 342 will preferably be chosen to be dielectric.

Figure 4:
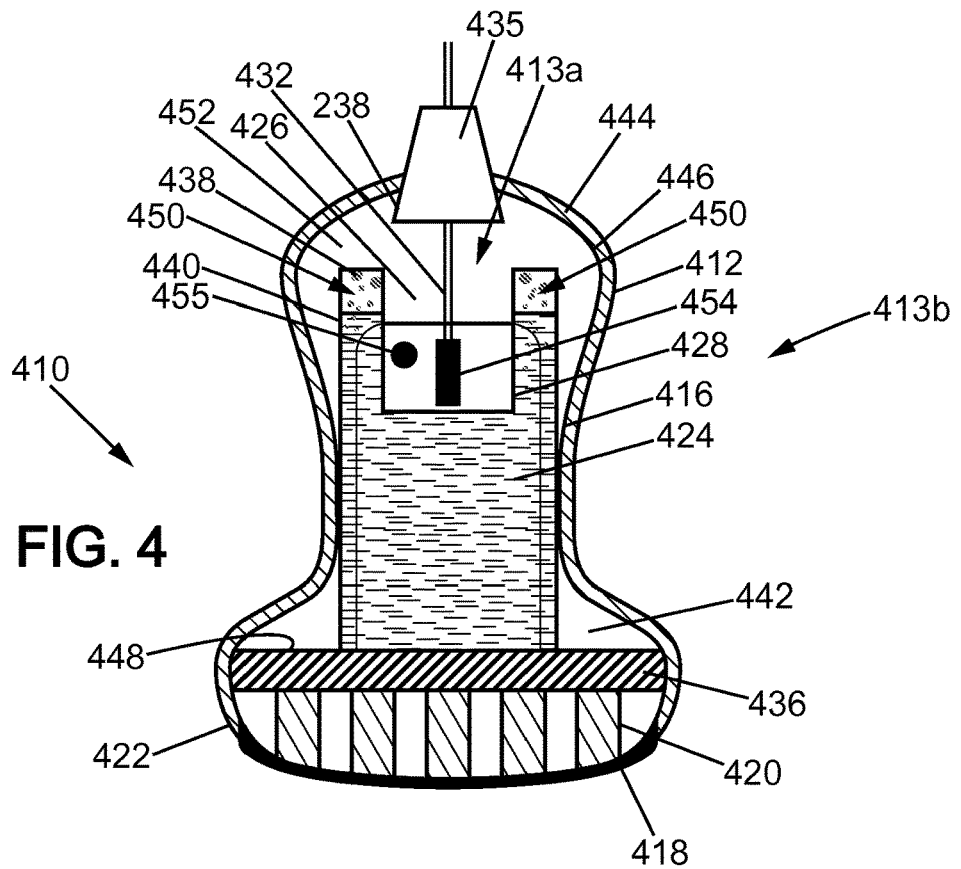
FIG. 4 is a front sectional view of a probe according to a fourth embodiment.
Figure 5:
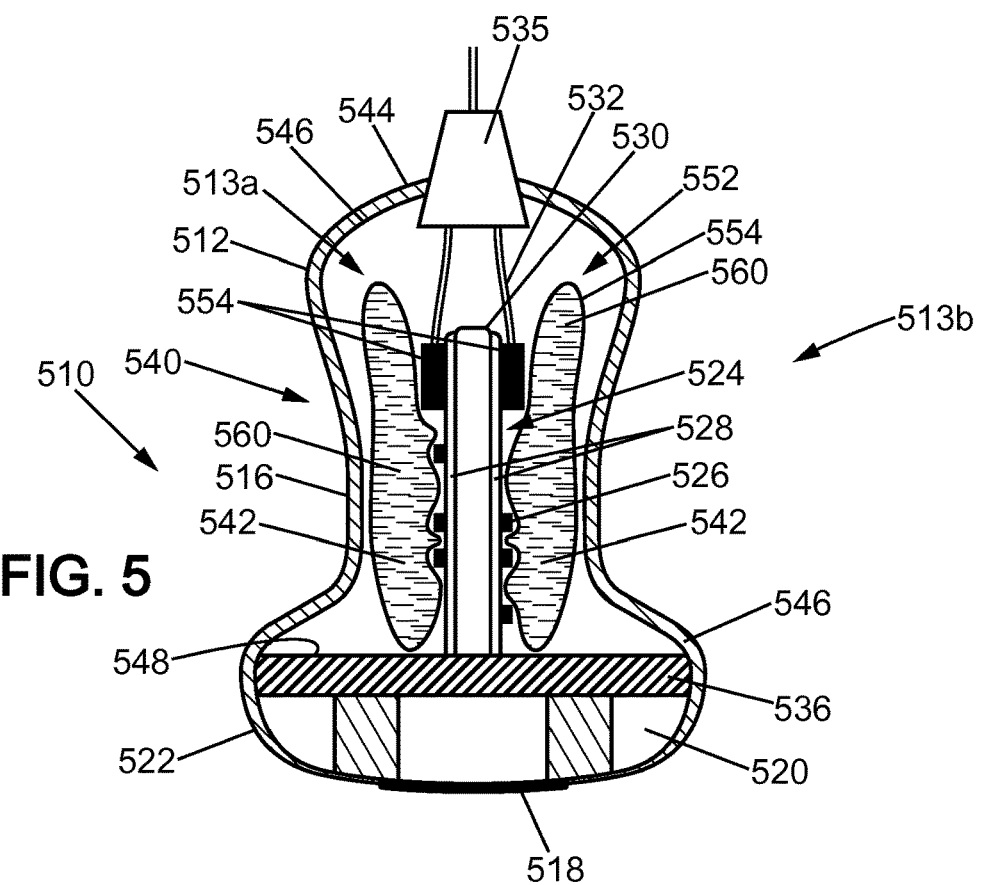
FIG. 5 is a lateral sectional view of a probe according to a fifth embodiment.

With respect to FIGS. 4 and 5, some embodiments of the probe showing cooling chambers not having the probe casing as a wall are illustrated. In these embodiments, the walls of the casing define a dry chamber and the cooling chamber is a sealed chamber contained in the dry chamber.

Thus, with reference to FIG. 4, probe 410 is similar to probes 110, 210, and 310, and has the alternatives of probes 110, 210, and 310. For brevity, the features that probe 410 has in common with probes 110, 210 and 310 will bear similar reference numbers but in the 400s, and will not be repeated here. In this embodiment, the inner wall 446 of the casing 412 defines the dry chamber 452. The cooling chamber 440 is located inside the dry chamber 452. A portion of the rear face 448 of the wave-blocking member 436 defines a wall of the cooling chamber 440. Alternatively, it is possible that the cooling chamber 440 has a wall which is in contact with the rear face 448 of the wave-blocking member 436. Also defining the cooling chamber 440 is a rigid wall 456 which skirts around the connections 454 to the coaxial cables 432. Alternatively, it is possible that the wall 456 is not rigid and/or that the wall does not skirt around the connections 454 to the coaxial cables 432. In the latter case, the heat transfer liquid 452 is chosen to be dielectric. Alternatively, it is possible that instead of one cooling chamber 440, the probe 410 has two or more cooling chambers 440. For example, the probe 410 may have one cooling chamber 440 connected to each side of the interface unit 424, similar to what is illustrated for the embodiment of FIG. 5.

FIG. 5 illustrates a variation of the embodiment of FIG. 4. Probe 510 is similar to probes 110, 210, 310, and 410, and has the alternatives of probes 110, 210, 310, and 410. Probe 510 differs from probe 410 in that the cooling chamber 540 is not partly defined by the rear face 548 of the wave-blocking element 536, but by a wall which may or may not be in contact with the rear face 548 of the wave-blocking element 536. Thus, the cooling chamber 540 comprises two flexible pouches 560 in contact with the printed circuits 528. The pouches 560 contain the heat transfer liquid 542 and are fluidtight to the heat transfer liquid 542 and/or to the gas. They may be entirely or partially filled with the heat transfer liquid 542, with or without partial filling with gas. The heat transfer liquid 542 may or may not be phase-changing, may or may not be dielectric, as discussed in the previous embodiments. The flexibility advantageously allows the pouches 560 to have a larger area of contact with the interface unit 524. However, it is conceivable that the pouches 560 may not be flexible. It is also conceivable that there is only one flexible pouch 560, or more than two flexible pouches 560. The flexible pouches may for example be in contact with the rear face 548 of the wave-blocking element 536 or may not, and the pouches may be of various shapes.

Optionally, in this embodiment, the casing 512 is not necessarily fluidtight since the pouches 560 themselves form fluidtight casings for the heat transfer liquid 142.

The probe of all the above embodiments can be manufactured according to the method set forth below.

In particular, in this manufacturing method:
a casing (112, 212, 312, 412, 512) is provided to define an interior (113a, 213a, 313a, 413a, 513a) of the probe (110, 210, 310, 410, 510),
one or more emitting and/or receiving elements for acoustic waves (120, 220, 320, 420, 520) are provided and they are placed at a first end (122, 222, 322, 422, 522) of the casing (110, 210, 310, 410, 510),
an interface unit (124, 224, 324, 424, 524) is provided and it is connected to the emitting and/or receiving element(s) (120, 220, 320, 420, 520), the interface unit (124, 224, 324, 424, 524) is placed in the interior (113a, 213a, 313a, 413a, 513a) of the casing (112, 212, 312, 412, 512),
the casing is sealed closed to form a sealed cooling chamber (140, 240, 340, 440, 540) arranged in the interior (113a, 213a, 313a, 413a, 513a) of the casing (112, 212, 312, 412, 512), the interface unit (124, 224, 324, 424, 524) being at least partially arranged in the cooling chamber (140, 240, 340, 440, 540) or in contact with the cooling chamber (140, 240, 340, 440, 540), and
the cooling chamber (140, 240, 340, 440, 540) is at least partially filled with a heat transfer liquid (142, 242, 342, 442, 542).

The filling of the cooling chamber with the heat transfer liquid can be carried out by any means. For example, one can use a syringe which penetrates through an elastic membrane on the casing, or heat transfer liquid to fill the cooling chamber can be supplied through a valve which can be closed.

Optionally, the cooling chamber (140, 240, 340, 440, 540) is filled with the heat transfer liquid (142, 242, 342, 442, 542) but also with a gas (150, 250, 350, 450). This filling with gas can be carried out simultaneously with, before, or after filling with the heat transfer liquid. This filling with gas may make use of the means for filling with heat transfer liquid or may have its own means for filling, meaning a separate means.

In addition, the casing may be made in several parts, for example in two parts. The casing can then be sealed closed by joining said two parts, for example with a means of gluing and/or of sealing.

Furthermore, as shown in FIG. 5, one or two flexible pouches 560 are used. In this case, the last two steps of the method (i.e. the steps of closing the casing and filling with heat transfer liquid) are carried out by the following successive steps:
at least one flexible pouch 560, at least partially filled (previously filled) with heat transfer liquid 542, is placed in the casing 512, and
the casing is sealed closed to form the sealed cooling chamber 540.

The pouch or pouches 560 are thus enclosed inside the interior of the casing within said cooling chamber for the probe.

The invention claimed is:

1. Probe, in particular for ultrasound, comprising:
a casing defining an interior of the probe,
one or more emitting and/or receiving elements for acoustic waves arranged at a first end of the probe,
an interface unit connected to the emitting and/or receiving element, the interface unit being located within the interior of the casing, wherein the probe comprises:
a sealed cooling chamber arranged within the interior of the casing, the interface unit being arranged at least partially in the cooling chamber or in contact with the cooling chamber, the cooling chamber being at least partially filled with a heat transfer liquid.

2. Probe according to claim 1, wherein the heat transfer liquid is dielectric.

3. Probe according to claim 1, wherein the heat transfer liquid is phase changing, and has a transition temperature that is a function of the temperature resulting from the heat produced by the emitting and/or receiving element for acoustic waves during operation.

4. Probe according to claim 3, wherein the transition temperature of the heat transfer liquid is between room temperature and a temperature of 90 degrees Celsius.

5. Probe according to claim 1, wherein the cooling chamber is filled with the heat transfer liquid and a gas.

6. Probe according to claims 1 to 5 claim 1, wherein the portion of the cooling chamber filled with the heat transfer liquid represents at least 5% of the volume of the cooling chamber.

7. Probe according to claim 1, comprising a pressure sensor and/or a temperature sensor within the interior of the probe.

8. Probe according to claim 1, comprising an acoustic-wave-blocking element arranged between the interface unit and said at least one emitting and/or receiving element for acoustic waves, the cooling chamber being in contact with the wave-blocking element.

9. Probe according to claim 1, comprising an acoustic-wave-blocking element arranged between the interface unit and said at least one emitting and/or receiving element for acoustic waves, the cooling chamber being defined by a rear face of the wave-blocking element and by an inner wall of the casing.

10. Probe according to one of claims 1 to 7 claim 1, wherein the interface unit is completely contained within the cooling chamber.

11. Probe according to claim 1, wherein the interface unit comprises an antenna.

12. Probe according to claim 1, wherein the interior of the probe comprises a dry chamber separate from the cooling chamber, the cooling chamber being proximal to the first end of the probe.

13. Probe according to claim 12, wherein a portion of the interface unit is arranged in the dry chamber.

14. Probe according to claim 1, wherein the sealed cooling chamber comprises at least one flexible portion.

15. Probe according to claim 1, wherein the cooling chamber comprises two flexible pouches at least partially filled with the heat transfer liquid.

16. Method of manufacturing a probe, in particular for ultrasound, wherein:
- a casing is provided to define an interior of the probe,
- one or more emitting and/or receiving elements for acoustic waves are provided and they are placed at a first end of the casing,
- an interface unit is provided and it is connected to the emitting and/or receiving element(s), the interface unit is placed within the interior of the casing,
- the casing is sealed closed to form a sealed cooling chamber arranged within the interior of the casing the interface unit being at least partially arranged in the cooling chamber or in contact with the cooling chamber, and
- the cooling chamber is at least partially filled with a heat transfer liquid.

17. Method according to claim 16, wherein the cooling chamber is filled with the heat transfer liquid and a gas.

18. Method according to claim 16, wherein the last two steps of the method are carried out by the following successive steps:
- a flexible pouch at least partially filled with the heat transfer liquid is placed in the casing,
- the casing is sealed closed to form the sealed cooling chamber.

* * * * *